US010898360B2

United States Patent
Farag Eells et al.

(10) Patent No.: US 10,898,360 B2
(45) Date of Patent: Jan. 26, 2021

(54) LOW PROFILE STEPPED DELIVERY SYSTEM

(71) Applicant: COOK MEDICAL TECHNOLOGIES LLC, Bloomington, IN (US)

(72) Inventors: Jacqueline Farag Eells, Bloomington, IN (US); Robert M. Eells, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 63 days.

(21) Appl. No.: 16/429,589

(22) Filed: Jun. 3, 2019

(65) Prior Publication Data
US 2019/0282386 A1    Sep. 19, 2019

Related U.S. Application Data

(60) Continuation of application No. 15/227,280, filed on Aug. 3, 2016, now Pat. No. 10,307,278, which is a
(Continued)

(51) Int. Cl.
*A61F 2/966* (2013.01)
*A61F 2/95* (2013.01)

(52) U.S. Cl.
CPC .......... *A61F 2/966* (2013.01); *A61F 2/95* (2013.01); *A61F 2/9517* (2020.05);
(Continued)

(58) Field of Classification Search
CPC .......... A61F 2002/011; A61F 2/2427; A61F 2/2436; A61F 2/2439; A61F 2/95;
(Continued)

(56) References Cited

U.S. PATENT DOCUMENTS 5,707,376 A    1/1998 Kavteladze et al.
5,749,920 A    5/1998 Quiachon et al.
(Continued)

FOREIGN PATENT DOCUMENTS

WO    WO 2008/017683 A1    2/2008

OTHER PUBLICATIONS

Extended European Search Report dated Feb. 12, 2014 for European Patent Application No. 13275269.2 (4 pages).

*Primary Examiner* — Wade Miles
(74) *Attorney, Agent, or Firm* — Brinks Gilson & Lione (57) ABSTRACT

A low profile stepped delivery system for retracting trigger wires from a prosthesis to release the prosthesis from a delivery device. A rod is disposed within an axial bore of a handle. The rod has a first longitudinal surface and a second longitudinal surface. A first engagement mechanism is disposed on the first longitudinal surface and a second engagement mechanism disposed on the second longitudinal surface. A wire coiling assembly is disposed at an end of the of the handle and comprises a first rotary gear that is adapted to be rotated by the first engagement mechanism, a second rotary gear that is adapted to be rotated by the second engagement mechanism, a first wire spool that is coupled to a rotation of the first rotary gear, and a second wire spool that is coupled to the rotation of second rotary gear. The first wire spool is configured to secure a first trigger wire and the second wire spool is configured to secure a second trigger wire.

9 Claims, 7 Drawing Sheets

Related U.S. Application Data division of application No. 14/064,651, filed on Oct. 28, 2013, now Pat. No. 9,539,130.

(60) Provisional application No. 61/719,599, filed on Oct. 29, 2012.

(52) U.S. Cl.
CPC ..... *A61F 2/9522* (2020.05); *A61F 2002/9511* (2013.01); *A61F 2002/9665* (2013.01)

(58) Field of Classification Search
CPC ...... A61F 2002/9505; A61F 2002/9511; A61F 2002/9517; A61F 2/962; A61F 2/966; A61F 2/9665
See application file for complete search history.

(56) References Cited

U.S. PATENT DOCUMENTS

| | | |
|---|---|---|
| 5,824,044 A | 10/1998 | Quiachon et al. |
| 5,968,052 A | 10/1999 | Sullivan, III et al. |
| 6,090,136 A | 7/2000 | McDonald et al. |
| 6,168,610 B1 | 1/2001 | Marin et al. |
| 6,322,587 B1 | 11/2001 | Quiachon et al. |
| 6,602,280 B2 | 8/2003 | Chobotov |
| 6,660,031 B2 | 12/2003 | Tran et al. |
| 6,755,854 B2 | 6/2004 | Gillick et al. |
| 7,052,511 B2 | 5/2006 | Weldon et al. |
| 7,122,050 B2 | 10/2006 | Randall et al. |
| 7,780,716 B2 | 8/2010 | Pappas et al. |
| 7,799,065 B2 | 9/2010 | Pappas |
| 2002/0151955 A1 | 10/2002 | Tran et al. |
| 2003/0191516 A1 | 10/2003 | Weldon et al. |
| 2004/0153137 A1 | 8/2004 | Gaschino et al. |
| 2005/0149159 A1 | 7/2005 | Andreas et al. |
| 2006/0142836 A1 | 6/2006 | Hartley et al. |
| 2006/0173524 A1 | 8/2006 | Salahieh et al. |
| 2006/0282150 A1 | 12/2006 | Olson et al. |
| 2007/0088421 A1 | 4/2007 | Loewen |
| 2007/0260301 A1 | 11/2007 | Chuter et al. |
| 2008/0082159 A1 | 4/2008 | Tseng et al. |
| 2008/0140178 A1 | 6/2008 | Rasmussen et al. |
| 2008/0319524 A1 | 12/2008 | Yachia et al. |
| 2009/0099638 A1 | 4/2009 | Grewe |
| 2011/0077666 A1 | 3/2011 | McCahon et al. |
| 2012/0158117 A1 | 6/2012 | Ryan |
| 2013/0184805 A1 | 7/2013 | Sawada |
| 2013/0274856 A1 | 10/2013 | Arbefeuille et al. |
| 2014/0025155 A1 | 1/2014 | Masubuchi |
| 2014/0180381 A1 | 6/2014 | Kelly |

Fig. 13

LOW PROFILE STEPPED DELIVERY SYSTEM

CROSS-REFERENCE TO RELATED APPLICATIONS

This application is a continuation of U.S. application Ser. No. 15/227,280 filed on Aug. 3, 2016, which is a divisional of U.S. application Ser. No. 14/064,651, filed on Oct. 28, 2013 and which claims priority to U.S. Provisional Application No. 61/719,599, filed Oct. 29, 2012, the contents of which are incorporated in their entirety.

BACKGROUND

This invention relates to medical devices and, in particular, to devices, systems, and methods for actuating a plurality of trigger wires for delivery of an endoluminal prosthesis, such as a stent graft delivered in a body lumen.

Deploying an endoluminal prosthesis into a vessel of a patient from a location outside the body is generally known. An endoluminal prosthesis, such as a stent or stent graft, is typically introduced into a vessel in a radially constrained state. Once the endoluminal prosthesis is positioned, it can then be deployed within the vessel by actuation of a trigger wire system.

An endoluminal prosthesis may be either self-expanding or balloon-expandable, or it can have characteristics of both types. A self-expanding endoluminal prosthesis may be delivered to a target site in a compressed configuration and subsequently expanded by removing a delivery sheath, removing trigger wires, and/or releasing diameter reducing ties. With a self-expanding endoluminal prosthesis, the endoluminal prosthesis expands primarily based on its own expansive force without the need for further mechanical expansion. In an endoluminal prosthesis made of a shape-memory alloy such as nitinol, the shape-memory alloy may be employed to cause the endoluminal prosthesis to return to a predetermined configuration upon removal of the sheath or other device maintaining the endoluminal prosthesis in its pre-deployment configuration.

When trigger wires are used as a deployment control mechanism for a stent graft, the trigger wires may releasably couple the proximal and/or distal ends of a stent to a delivery catheter. For example, one or more trigger wires may be used to retain a stent graft at one or both ends to a delivery device. For example, one or more trigger wires may be looped through a portion of a stent or the graft at one or both ends of the prosthesis prosthesis. For example, a stent graft may have proximal and/distal stents having apices. The trigger wires may be disposed through, and pull upon, one or more of the apices to pull the stent closely against the delivery catheter. Alternatively, the trigger wires may run through one or more sutures which are attached to one or more apices of the stent, such as disclosed and shown in U.S. Publication No. 2008/0140178, and in particular FIGS. 3-8 and accompanying text, which disclosure is incorporated by reference in its entirety.

An endoluminal prosthesis is typically introduced into a vessel via a delivery device. Such a delivery device may include a cover or sheath that covers the endoluminal prosthesis. The sheath covering the endoluminal prosthesis is then manipulated within the vessel to a target location for deployment. The sheath is retracted such that it no longer covers the endoluminal prosthesis, allowing the endoluminal prosthesis to expand. The sheath is typically retracted by manually pulling the sheath back in a distal direction. The sheath may also be retracted through the use of at least one trigger wire. The trigger wire may pull on the sheath.

Trigger wires extending from a distal end of the delivery device to the prosthesis may then be retracted by simply pulling on them to release the ends of the prosthesis from the delivery device. The trigger wires can be manipulated from the distal end of the delivery device.

SUMMARY

The present disclosure provides a system to actuate trigger wires in a delivery device. The system includes a handle having a proximal end, a distal end, and an axial bore through the handle. A rod is slideably disposed within the axial bore. The rod has a proximal end, a distal end, a first longitudinal surface, and a second longitudinal surface. A first engagement mechanism is disposed on the first longitudinal surface and a second engagement mechanism is disposed on the second longitudinal surface. A wire coiling assembly is disposed at the distal end of the of the handle and comprises a first rotary gear that is adapted to be rotated by the first engagement mechanism, a second rotary gear that is adapted to be rotated by the second engagement mechanism, a first wire spool that is coupled to a rotation of the first rotary gear, and a second wire spool that is coupled to the rotation of second rotary gear. The first wire spool is configured to secure a first trigger wire and the second wire spool is configured to secure a second trigger wire.

In another example, a system for delivering an endoluminal prosthesis is described. The system includes a handle having a handle proximal end, a handle distal end, and a longitudinal bore. An elongated tubular member is secured to the handle. The elongated tubular member has a tubular member proximal end, a tubular member distal end, and at least one lumen between the tubular member proximal end and the tubular member distal end. A sheath is disposed at the tubular member proximal end and the sheath is configured to slide about the elongated tubular member in a longitude direction. An endoluminal prosthesis is disposed at the tubular member proximal end and the endoluminal prosthesis is radially constrained by the sheath. A first trigger wire extends from the handle through the at least one lumen to the proximal end of the elongated tubular member. The first trigger wire retains the proximal end of the prosthesis on the delivery device. A second trigger wire may extend from the handle through the at least one lumen to the distal end of the elongated tubular member. The second trigger wire retains the distal end of the endoluminal prosthesis on the delivery device. A wire coiling assembly is disposed in the distal end of the handle. The wire coiling assembly includes a rod having a first surface having a first plurality of teeth and a second surface having a second plurality of teeth, and a coiling mechanism comprising a first gear configured to engage the first plurality of teeth, a second gear configured to engage the second plurality of teeth, a first spool securing the first trigger wire and coupled to the rotation of the first gear, and a second spool securing the second trigger wire and coupled to the rotation of the second gear.

A toothed rod, usable in a rack and pinion assembly, may be used in the endoluminal prosthetic deployment system disclosed. The rod has a distal handle. Between the distal end and the proximal end, a first surface is disposed. The first surface has a first portion disposed proximate the proximal end with teeth and a first smooth portion disposed proximate the distal end. A second surface is disposed between the distal end and the proximal end. The second surface has a second smooth portion disposed proximate the distal end, a third smooth portion disposed proximate the proximal end, and a second portion having teeth disposed between the second smooth portion and the third smooth portion. The trigger wire system may further have one or more trigger wires attached to the sheath and adapted to slide the sheath relative to the endoluminal prosthesis.

BRIEF DESCRIPTION OF THE DRAWINGS

To further clarify the above and other advantages and features of the one or more present inventions, reference to specific embodiments thereof are illustrated in the appended drawings. The drawings are exemplary are therefore not to be considered limiting.

DETAILED DESCRIPTION

In the present application, the term "proximal" refers to a direction that is generally closest to the heart during a medical procedure, while the term "distal" refers to a direction that is furthest from the heart during a medical procedure. To further clarify, the proximal end of a delivery device is that end that is disposed within the patient and the distal end is that end outside of the patient during a procedure.

The term "prosthesis" means any device, object, or structure that supports, repairs, or replaces, or is configured to support, repair, or replace a body part or a function of that body part. It can also mean a device that enhances or adds functionality to a physiological system. Examples of prostheses include stents, stent grafts, vessel occlusion devices, vena cava filters, and the like.

The term "stent" means any device or structure that provides, or is configured to provide, rigidity, expansion force, or support to a body part (e.g., a diseased, damaged, or otherwise compromised body lumen.). A stent may comprise any suitable material, including, but not limited to, biocompatible metals and plastics. Examples of suitable materials include metals such as stainless steel and NITI-NOL, and plastics such as polyethylene terephthalate ("PET"), polytetrafluoroethylene ("PTFE") and polyurethane.

A stent may be "expandable," that is, it may be capable of being expanded from a constricted configuration to an expanded configuration. A stent may be self-expanding and expand by virtue of its own resilience. Alternatively, a stent may be pressure-expandable and expand only upon the application of an external force. In addition, a stent may be expandable upon application of heat, such as when exposed to body temperature. An example of a self-expanding stent is the Z-STENT®, which is available from Cook Incorporated, Bloomington, Ind., USA.

The term "lumen" describes a cavity or channel within a tube or a tubular body, such as body vessel. The term "endoluminal" means within a lumen, and can refer to objects that are found or that can be placed within a lumen, or methods or processes that occur within a lumen. An "endoluminal prosthesis" is thus a prosthesis that is found, or that can be placed, within a lumen. Examples of endoluminal prostheses include, but are not limited to, stents, grafts, stent grafts, venous or aortal valves, and vena cava filters. An endoluminal prosthesis may be generally tubular and comprise one or more lumens. Examples of tubular prostheses include straight, branched, and bifurcated prostheses.

Described is a handle for a trigger wire actuation mechanism for a prosthesis delivery device. In operation, a proximal end of the delivery device is introduced into a patient's vessel and guided to a delivery location. The distal end remains external to the patient and provides a control handle for the delivery device. As described further below, the delivery device has a prosthesis retained on the delivery device by one or more trigger wires and held, prior to delivery, in a compressed condition by a retractable sheath. The prosthesis may be a stent or stent-graft or other medical device for which trigger wires are used to retain the device on and release it from the delivery device. Exemplary prostheses are expandable stents and stent grafts.

Figures 1, 2, 3:
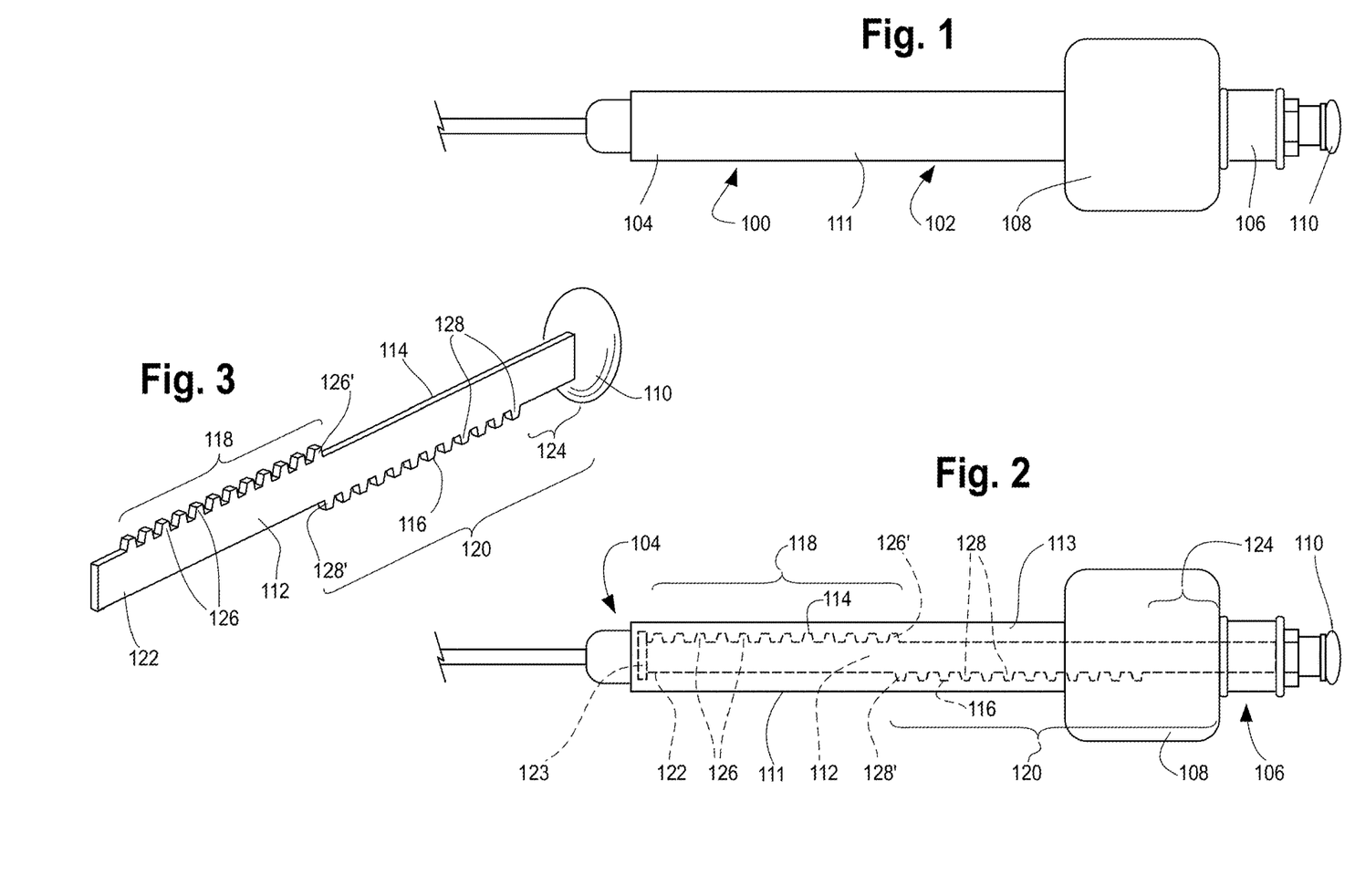
FIG. 1 shows an example of a handle of a delivery device for an endoluminal prosthesis.
FIG. 2 shows the handle of FIG. 1 with a portion of a trigger wire actuation mechanism disposed within the lumen of the handle.
FIG. 3 shows an exemplary rod or rack mechanism of a trigger wire actuation mechanism.

FIG. 1 shows a portion of an exemplary delivery device 100, and in particular a delivery device handle 102. The handle 102 is configured to be disposed at or near the distal end (not shown) of the delivery device 100. The handle has a proximal end 104, a distal end 106 and actuation knob or handle 110. A trigger wire actuation mechanism housing 108 is disposed at the distal end of the handle 102 The handle 102 has an elongated member 111 having at least one lumen 113 between the proximal end 104 of the handle 102 and the distal end 106 of the handle 102. The housing 108 may have a diameter of 0.5 to 1.5 inches, preferably about 1 inch, and a length of 0.2 to 1 inch, preferably about 0.5 inches. The actuation knob/handle 110 is about 0.1 to 0.3 inches in diameter and preferably about 0.2 inches in diameter.

As shown in FIG. 2, a track system, such as an elongate trigger wire actuation rod 112 is disposed in the lumen 113 of the handle 102. The rod 112 extends substantially for the length of the lumen of the handle 102. As shown, the rod 112 may be in the form of a rack, which is configured to engage one or more gears (not shown in FIGS. 1 and 2). The rod 112 has an upper surface 114, a lower surface 116, a proximal region 118, a distal region 120, a proximal end 122 including a proximal hub 123, and a distal end portion 124. The rod 112, in an exemplary handle, may be 2 to 4 inches long and preferably about 3 inches long. The rod 112 may have a diameter of 0.2 to 0.5 inches, and preferably about 0.35 inches. The rod 112 may have teeth 126, 128 on either or both of the upper surface 114 and the lower surface 116.

As shown in FIG. 3, the rod 112 may have upper teeth 126 and lower teeth 128. In this example, the upper teeth 126 extend along the upper surface 114 only in the area of the proximal region 118 and the lower teeth 128 extend along the lower surface 116 only in the area of the distal region 120, such that the distal most upper tooth 126' ends approximately where the proximal most lower tooth 128' begins. There may be some overlap of these regions. Although the rod 112 is shown with the upper teeth 126 in the proximal region 118 and the lower teeth 128 in the distal region 120, the opposite configuration may also be used. The length of each of the proximal 118 and distal 120 regions may each be 2-4 cm long, and preferably about 3 cm long. The distal end region 124 preferably has no teeth and is of sufficient length to extend through the housing 108 and out the distal end 106 of the handle.

Figure 4:
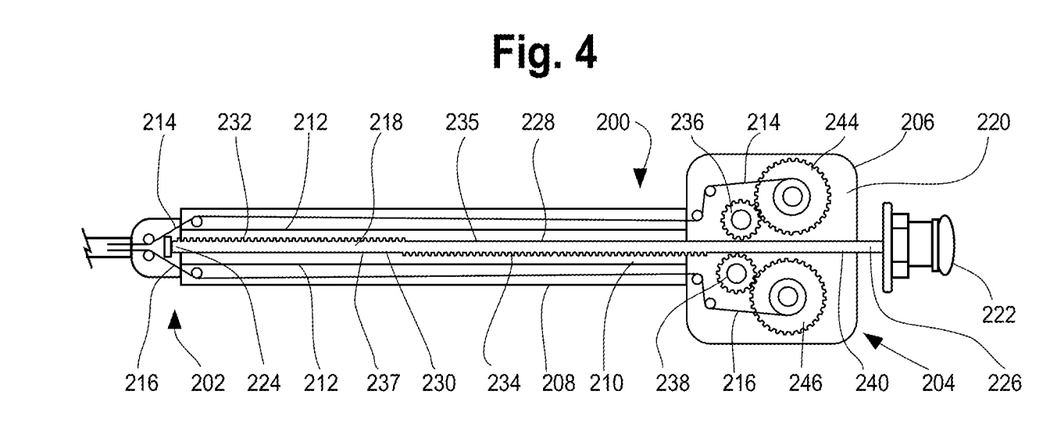
FIG. 4 shows an exemplary handle with an exemplary trigger wire actuation mechanism before the trigger wires have been released.
Figure 5:
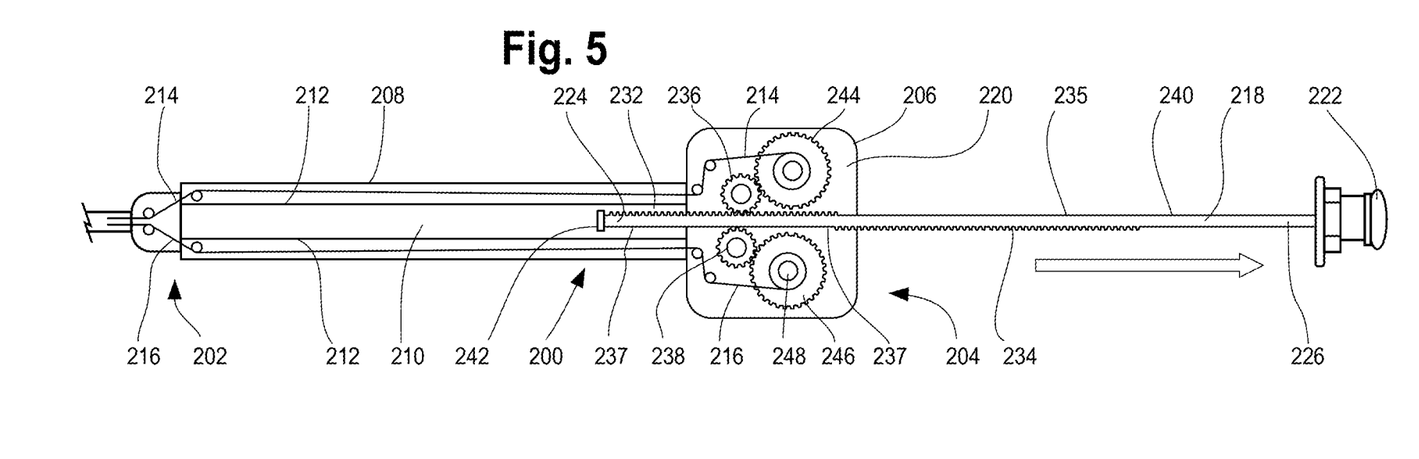
FIG. 5 shows the mechanism of FIG. 4 where at least one of the trigger wires has been released.

FIGS. 4 and 5 show an exemplary handle for a prosthesis delivery device having a track and gear (for example, a rack and pinion) trigger wire actuation system. The gears and track may be of any suitable material, but are preferably formed of a very hard plastic such as Delrin. As set forth above, prosthesis delivery systems may use one or more trigger wires to retain either or both the proximal and distal ends of the prosthesis to the delivery system until it is desirable to release the prosthesis from the delivery system. In one example, a proximal trigger wire system, with one or more trigger wires, retains the proximal end of the prosthesis to a proximal retention region or point on the delivery system, and a separate distal trigger wire system, with one or more trigger wires, retains the distal end of the prosthesis to a distal retention region or point on the delivery system. In some examples, it may be desirable to retain a single end of the prosthesis, such as shown in U.S. Publication No. 2006/0142836, which disclosure is incorporated by reference herein in its entirety. In other examples, one trigger wire, or one set of trigger wires may be used to retain both ends of the prosthesis, such as shown in U.S. Publication No. 2008/0140178, which disclosure is incorporated by reference herein in its entirety.

The trigger wire or wires may, for example, engage the graft material of a stent graft prosthesis at either or both ends either directly or indirectly or engage proximal most and distal most stents on the prosthesis either directly or indirectly. For example, one or more trigger wires may directly engage stent ends or apices and draw them inward into the delivery device such as shown in FIG. 14 of U.S. Publication No. 2006/0142836, which disclosure is incorporated by reference herein in its entirety, or may engage threads or sutures that engage the stent end or apices, such as shown in FIGS. 5-8 of U.S. Publication No. 2008/0140178 and FIGS. 14-17 of U.S. Publication No. 2006/0142836, which disclosure is incorporated by reference herein in its entirety. As set forth above, one trigger wire may be used for each, or either end, such as that shown in FIG. 13 of U.S. Publication No. 2006/0142836, which disclosure is incorporated by reference herein in its entirety, or multiple trigger wires such as FIG. 12 of U.S. Publication No. 2006/0142836, which disclosure is incorporated by reference herein in its entirety.

FIGS. 4 and 5 show an exemplary handle for a prosthesis delivery device having a track and gear (for example, a rack and pinion) trigger wire actuation system. Handle 200 is configured to be located at or near a distal end of a delivery system. Handle 200 has a proximal end 202, a distal end 204, a trigger wire actuation mechanism housing 206, and an elongate proximal portion 208. Elongate proximal portion 208 has a central lumen 210 extending therethrough. Elongate proximal portion 208 may also have a separate track or lumen 212 for one or more guidewires 214, 216. Elongate proximal portion 208 may be cylindrical and may include a grip, such as that shown in FIG. 6, and also may include a greater diameter proximal end, such as that shown in FIG. 6. The increased diameter provides a gripping point for a user. The proximal end 202 of the handle 200 is sized and shaped to be attached to a delivery device. Such attachment may include a threaded portion, a press fit attachment, a plastic weld, a barb, or other type of attachment as known in the art. Disposed within the central lumen 210 is track/rod, such as that described above with respect to FIGS. 2 and 3.

Shown in the example of FIGS. 4 and 5, disposed within the trigger wire actuation mechanism housing 206 is a trigger wire winding or coiling assembly 220. The housing 206 may have a diameter greater than a diameter elongate proximal portion 208 and houses the mechanical components of the trigger wire coiling assembly 220, described further below. The rod 218 is disposed longitudinally within central lumen 210 and extends past the wire coiling assembly 220 and out of the distal end 204 of the handle 200. The distal end of the rod 218 has a gripping handle 222 for manipulating the rod 218.

The mechanical components contained within the wire coiling assembly 220 are configured to convert a linear motion of the rod 218 into a winding action of the trigger wires 214, 216. These mechanical components provide a mechanical advantage allowing the trigger wires 214, 216 to release one or both ends of the prosthesis with less force than is otherwise possible by mere pulling on the trigger wires. In one embodiment, a three to one mechanical advantage gives an optimum combination of travel of the rod 218 and reduced force for retraction of the trigger wires and full deployment of the prosthesis. In another example, one of the trigger wire mechanisms, rather than retracting trigger wire, may be used to retract the retractable sheath that is disposed over the prosthesis. In this case, one or more trigger wires are attached to the sheath and retraction of the trigger wires causes distal retraction of the sheath from over a prosthesis to expose the prosthesis.

FIGS. 4 and 5 show one exemplary trigger wire actuation assembly. As shown in these FIGS. 4 and 5 and shown and described with regard to FIGS. 2 and 3, the rod 218 has a proximal end 224, a distal end 226, and two opposing sides 228, 230 at two opposing angular orientations. The proximal end 224 remains disposed within central lumen 210 of the handle. The two sides 228, 230 may be an upper surface and a lower surface, respectively, of the rod 218, or may be any substantially opposing side surfaces. The upper surface 228 of the rod 218 has a row of gear teeth 232 and the bottom surface 230 of the rod 218 has another row of gear teeth 234. The gear teeth 232, 234 are sized and shaped to interact with a respective drive gear 236, 238. In the embodiment of FIGS. 4 and 5, the gear teeth 232, 234 are the same size and shape on each surface but need not be.

As shown in FIGS. 2, 3, 4 and 5, the upper surface gear teeth 232 are disposed on a proximal portion (FIG. 3, numeral 118) of the rod 218 and the lower surface gear teeth 234 are disposed on a distal portion (FIG. 3, numeral 120) of the rod 218. As shown, the upper surface 228 has a smooth or blank portion 235 corresponding to the toothed lower surface and the lower surface 230 has a smooth or blank portion 237 corresponding with the toothed upper surface. The toothed regions may be of the same length, or may be of different lengths depending on the application. A region 240 of the rod 218 distal to the distal portion, and ending in the grip 222 has smooth or blank upper and lower surfaces so that this region does not engage the gear teeth.

As shown, this region 240 must be of sufficient length to extend through the gears and out of the housing. The proximal end of the rod may be provided with a hub or stop 242 to prevent the rod 218 from being fully removed from the handle. In other instances, the rod 218 may not have a stop and may be completely removed.

The mechanical components of the housing 220 may include two sets of gears including a set of drive gears 236, 238 and a set of spool gears 244, 246. Each set of gears corresponds to one of the rod surfaces. The sets of gears are selected to provide a desired mechanical advantage. In the example of FIGS. 4 and 5, the spool gears 244, 246 have a radius three times greater than a radius of the drive gears 236, 238 resulting in a 3 to 1 mechanical advantage. The drive gears translate the longitudinal movement of the rod out to torque, which is then translated to the larger spool gear with a 3:1 ratio to the drive gear. The spool gear winds the trigger wire with three times the torque of the drive gear. In other configurations, the gear ratio may be different and may be different for each set of gears. For example the gear ratio may be 2:1 to 4:1.

As shown in FIGS. 4 and 5, trigger wires 214, 216 (or sets of trigger wires) are wound onto their respective spool gear 244, 246. A large metal pin 248 at the center of each spool gear will attach the wires to the spool gear.

The gears are considered to be coupled in rotation if the rotation of one gear causes a rotation in a corresponding gear. For example, the perimeter of the gears may interact coupling their rotation, or they could be coupled about a common axis and rotate at the same angular velocity. FIGS. 4 and 5 illustrate gears 236, 238, 244, 246 that have parallel axes of rotation, with each axis of rotation being perpendicular to the longitudinal axis of the rod 218.

Figure 7:
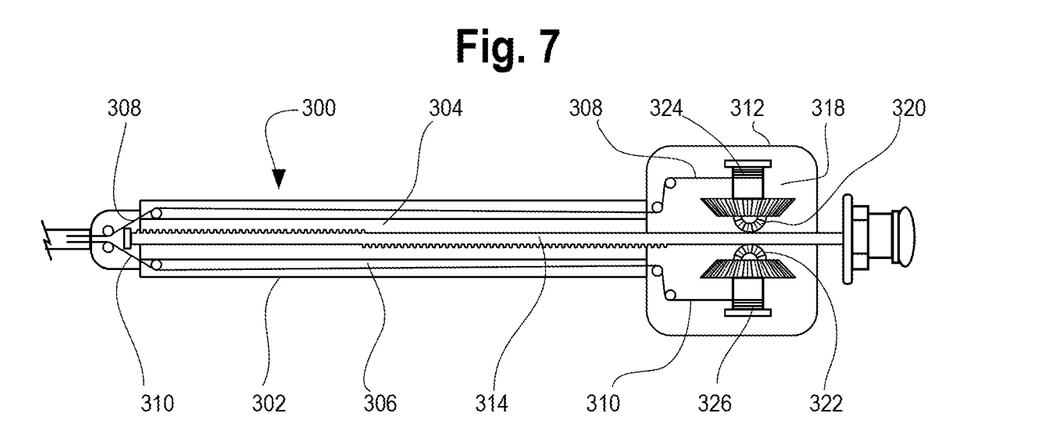
FIG. 7 shows another alternative trigger wire actuation mechanism.

FIG. 7 illustrates another example of a handle 300. As with FIGS. 4 and 5, handle 300 has and elongate proximal portion 302, a central lumen 304, at least one trigger wire lumen 306, trigger wires 308, 310, gear housing 312, and rod 314. In the example of FIG. 7, a wire coiling assembly 318 is illustrated where the sets of gears include driving gears 320, 322 and spool gears 324, 326, which are beveled and orientated such that their respective axis of rotation are perpendicular to one another. Such a configuration has the added advantage of maintaining a lower profile than the configuration of FIGS. 4 and 5, because the larger gear is horizontal and presents a narrow profile. Further the bevel gears can be used to change directions.

Figure 6:
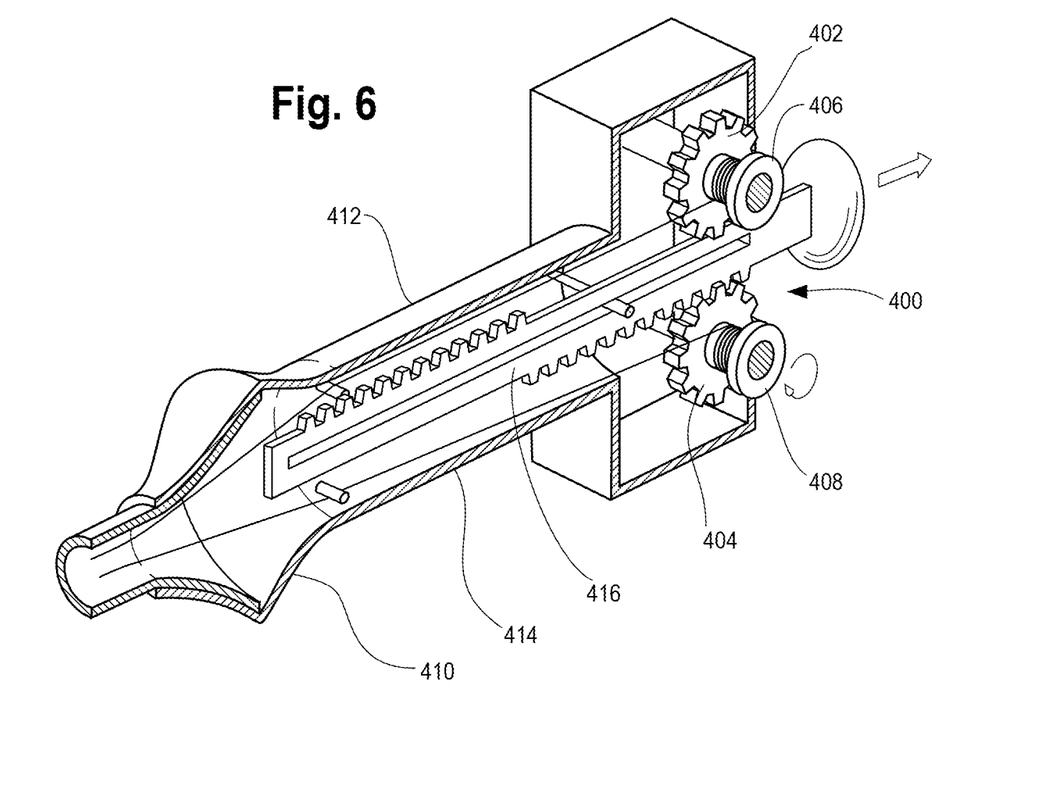
FIG. 6 shows an alternative trigger wire actuation mechanism.

As shown in FIG. 6, a wire coiling assembly 400 is illustrated in which driving gears 402, 404 are integrated with spools 406, 408. The mechanical advantage of the system can be adjusted by varying the ratio of the radius of the driving gears 402, 404 to the radius of the spool 406, 408. As shown in FIG. 6, the proximal end 410 of the handle 412 may have a larger diameter than the elongate portion 414 of the handle to provide a gripping point. Although not shown in FIG. 6, as shown in FIGS. 4, 5 and 7, one or more separate lumens may be provided for the trigger wires to prevent tangling with the rod 416.

A shown in the FIGS. 6 AND 7, as discussed above, the rod has a row of teeth on one surface and a row of teeth on a second surface. The row of the teeth on the first surface starts at or near the proximal end of the rod and extends to an intermediate point on the rod and the second row of teeth extends the intermediate point on the rod toward the distal end. Distally beyond the second row of teeth, the rod has a smooth surface that does not engage with the drive gear.

Figure 8:
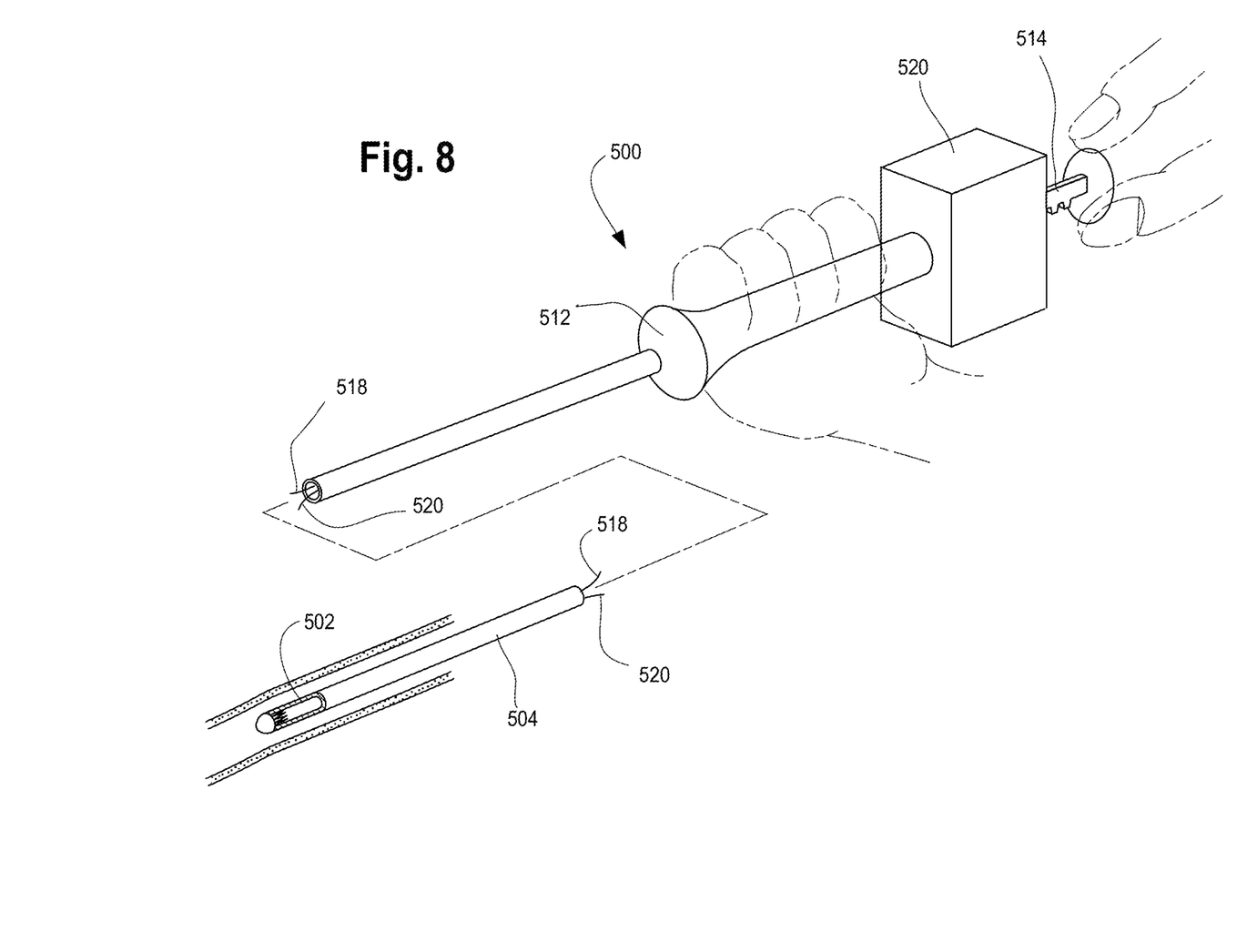
FIG. 8 shows a perspective view of an exemplary delivery device.
Figure 9:
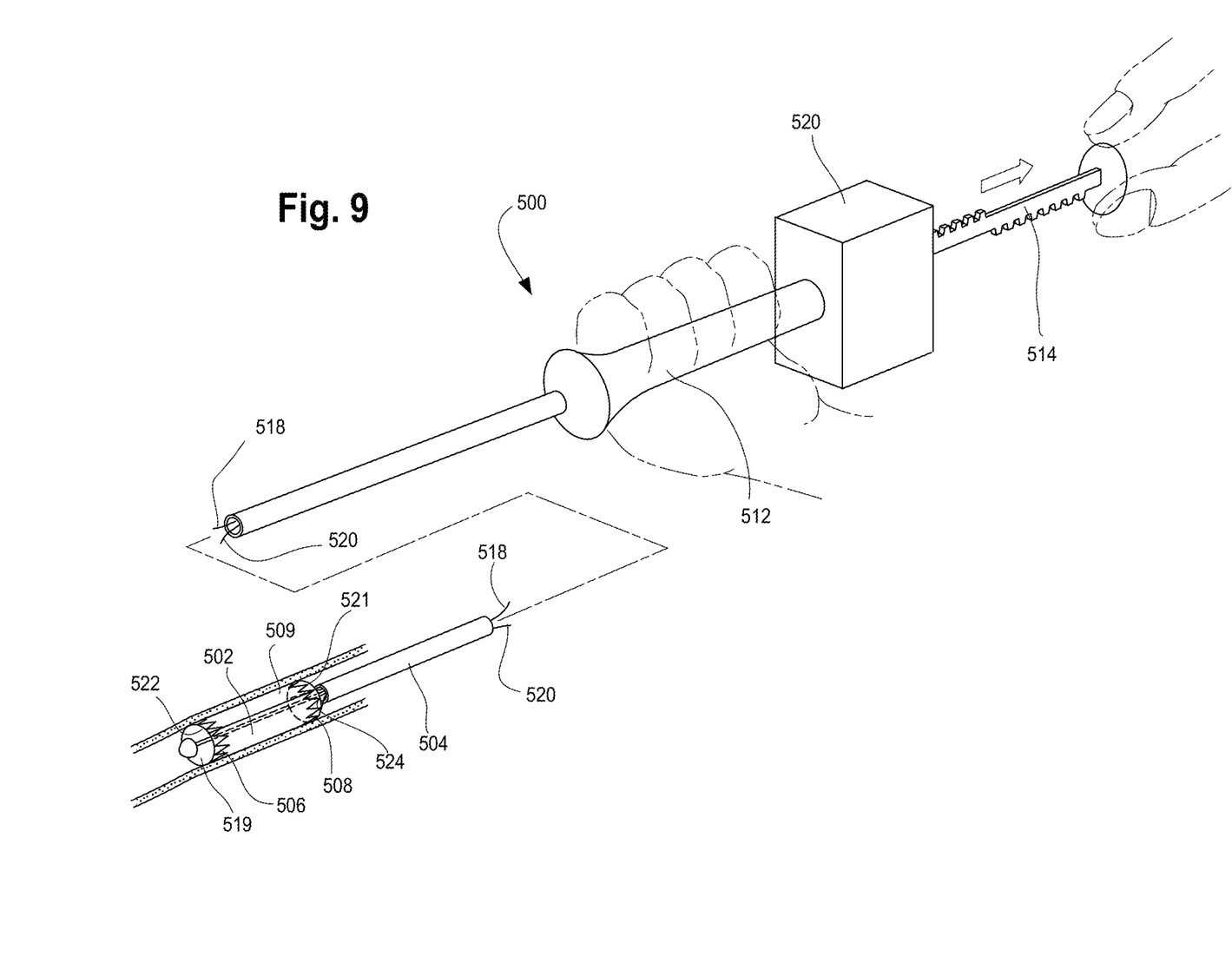
FIG. 9 shows a perspective view of the device of FIG. 8 where the sheath has been withdrawn from the prosthesis and the trigger wires retracted.

Operation of the trigger wire actuation system will now be described with reference to FIGS. 4, 5, 8, and 9. In FIGS. 8 and 9, a prosthesis delivery system 500 is shown. A prosthesis 502 is disposed on the device and covered initially by sheath 504. The prosthesis may have one or more stents such as a proximal end stent 506 and a distal end stent 508 disposed on and/or in a tube of graft material 509. The stents may have apices 510 as shown in FIG. 9. The sheath 504 is retractable from the prosthesis and may be connected to handle 512. Upon retraction of the sheath 504, by either moving the sheath 504 manually distally or advancing the rod 514 in the direction of the arrow in FIG. 9 to retract a trigger wire and coil it onto its respective spool gear, the prosthesis is exposed and allowed to at least partially expand.

In either case, once the sheath 504 is withdrawn, one or both ends of the prosthesis remain retained on the device by one or more trigger wire retention systems. For example, trigger wires 518, 520, which extend from the housing 520 to may be attached each to one end of the prosthesis to retain it onto the delivery device until the ends are released. As shown in FIG. 9, trigger wire 518 is attached to the proximal end 519 of the prosthesis 502 at attachment point 522 and trigger wire 520 is attached to the distal end 521 of the prosthesis 502 at attachment point 524. To release the ends of the prosthesis, the handle 516 of the rod is pulled distally and as the first row of teeth engages is respective drive gear, rotates the drive gear, which rotates it's corresponding spool gear to wind the trigger wire 518, 520 onto the spool gear (not shown) and release the trigger wire from its respective end of the prosthesis. Each spool gear may have a large center pin to which the trigger wire is attached and onto which it winds. As the rod 514 is pulled further, the second drive gear engages the second row of teeth, rotates the second drive gear and the corresponding spool gear to wind the second trigger wire onto the second spool gear thereby releasing the second trigger wire from its respective end of the prosthesis.

Referring again to FIGS. 4 and 5, the rod 218 is initially positioned inside the handle 200 with the distal end of the rod 218 near the distal portion end of the handle 200 and the proximal end of the rod 218 near the proximal end of the handle 200. Thus, when the rod 218 is moved from its initial position in a distal direction as indicated by the arrow in FIG. 5, the drive gear 236 corresponding to the upper surface 228 does not rotate until the row of teeth 232 engages the drive gear 236. This allows the rod 218 to be moved axially initially without rotating the drive gear 236. After the rod 218 has moved a predetermined distance, the row of teeth 232 will engage the drive gear 236 causing it to rotate with further movement of the rod 218.

On the lower surface 230 of the rod 218, the row of teeth 234 starts near the distal portion of the rod and extend towards the center of the rod 218. The proximal portion of the rod has a smooth surface such that it will not drive its corresponding drive gear 238. When the rod 218 is initially moved in the distal direction, the row of teeth 234 on the lower surface 230 of the rod 218 drive the corresponding drive gear 238 before the row of teeth 232 on the upper side 228 drive the corresponding drive gear 236. The lengths of the rows of teeth may be the same or different depending on the requirements of the delivery device. For example, if a delivery mechanism requires a long length of travel for one trigger wire versus another, the length of the corresponding row of teeth is extended. Another example of a delivery device that requires a longer amount of travel is a delivery device with a sheath that is retracted by one of the trigger wires. Alternatively, if the delivery device does not require a long travel, the length of the row of teeth may be shorter.

As set forth above, the rows of teeth may be such that they do not overlap and one row starts where the other ends. In other examples, the rows may overlap at some point such that both rows drive their corresponding gears simultaneously for some length. It is also possible that a portion of the rod may have no geared teeth between the finish of one row and the start of the other such that no corresponding drive gears are driven for that portion of the rod. By varying the starting and ending position of the rows of teeth, the trigger wires can have a staggered activation with one movement of the rod. Although the examples described are directed to pulling the rod distally, devices where the rod is pushed into the device, thereby rotating gear sets and retracting trigger wires are also contemplated.

As shown in the FIGS. 3-7, the rod has an upper surface and a lower surface at opposite angular orientations, but other configurations are contemplated. For example, the rod may have a polygonal cross section with a different track on each side of the polygon. A rod having a triangular cross section would have three longitudinal surfaces at three different angular orientations that could have three separate rows of teeth. By varying the relative positioning of the rows of teeth, the triggering sequence of the trigger wires can be easily controlled.

The rod may have an engagement mechanism other than geared teeth. For example, the rod may have a flat surface with a friction enhancement for interacting with a smooth wheel. In some embodiments, the set of gears may be toothless, in which friction between the gears causes rotation, and in still other embodiments, the sets of gears may have a pulley type arrangement.

In other arrangements, the rod has a third longitudinal surface disposed at a third angular orientation between the proximal rod end and the distal rod end, the third longitudinal surface having a third engagement mechanism disposed on the third longitudinal surface. In this arrangement, the wire coiling assembly further comprises a third rotary gear linked to an axial movement of the third engagement mechanism and a third wire spool coupled to the rotation of the third rotary gear, where the third wire spool is secured to a third trigger wire which is wound onto the third wire spool.

In one preferred device, as the rod is pulled distally, a first trigger wire or set of trigger wires is retracted and wound on to its spool until the proximal end of the trigger wire disengages from the proximal end of a restrained prosthesis, thereby releasing the proximal end of the prosthesis from the delivery device. Thereafter, as the rod is pulled further distally, a second trigger wire or set of trigger wires is retracted and wound on to its spool until the proximal end of the second trigger wire disengages from the distal end of the graft, thereby releasing the distal end of the prosthesis from the delivery device. In another preferred device, the trigger wires are attached such that the distal end of the prosthesis is released first by retraction of the first trigger wire or set of trigger wires and the proximal end of the prosthesis is thereafter released by retraction of the second trigger wire or set of trigger wires.

FIGS. 10-13, show one example of how the trigger wires may engage a prosthesis 600 at the proximal end 602 of delivery device 604 having a handle and trigger wire mechanism as previously described (not shown). As shown, delivery device proximal end 602, has a pusher 606, and inner cannula 608, a tapered nose cone dilator 610. Prosthesis 600 is disposed on the delivery device 604 and has a distal end 612 and a proximal end 614. The inner cannula 608 is at least partially disposed through a lumen 616 of the pusher 606. As shown in this example, pusher 606 has a pair of distal bores 617, 618 that extend from the lumen 616 and through the wall of the pusher 606. A pair of proximal bores 620, 622 extend from a lumen at the proximal end and through the wall of the proximal end of the delivery device.

Figure 10:
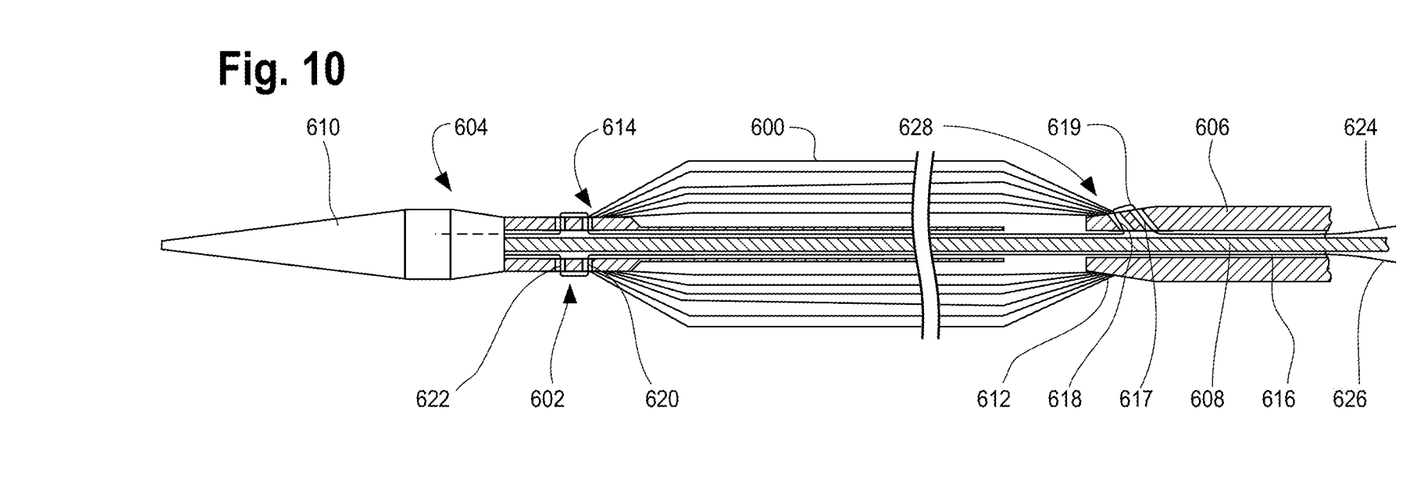
FIG. 10 shows a proximal end of a delivery device.

One or more trigger wires 624, 626 extends from the handle mechanism as described above and through the lumen 616 until it reaches bore distal bore 617, at which point it exits bore 617 and engages the distal end 612 of the prosthesis 600 or a trigger wire engagement mechanism 619, such as a suture loop or the like, at the distal end of the prosthesis 600 at a distal attachment region 628. The trigger wire 624 may be a single wire or more than one wire, and preferably three. The distal trigger wire 624 then re-enters the lumen through bore distal bore 618.

A similar trigger wire system is at the proximal end 614 of the prosthesis 600. One or more proximal trigger wires 626, preferably three, extend through lumen 616 and through the prosthesis 600 and exit through proximal bore 620. The wire or wires then engage the proximal end 614 or a trigger wire engagement mechanism (not shown) at the proximal end 614 of the prosthesis, then re-enter the device through proximal bore 622. The wire or wires may extend for a length into the nose cone 610.

Figure 11:
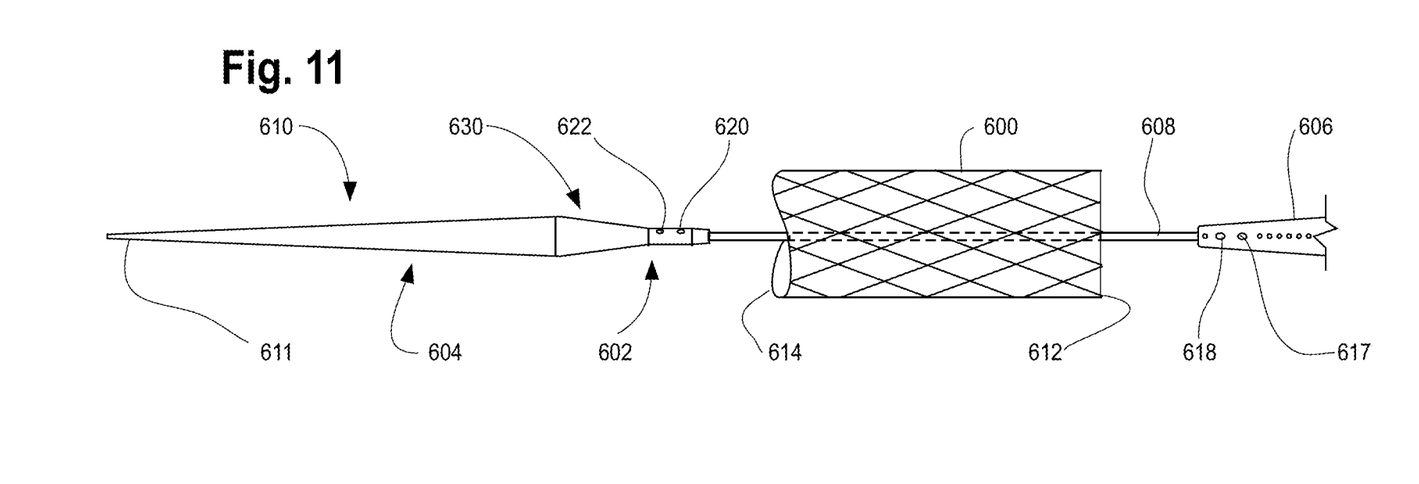
FIG. 11 shows another view of a proximal end of a delivery device.

FIG. 11 shows the proximal end 614 of the delivery device after the trigger wires have been retracted by the trigger wire retraction mechanism (not shown) and the prosthesis 600 expanded. As shown, the proximal end 614 has a nose cone dilator 610, which has a reverse taper 630, inner cannula 608, pusher 606, distal bores 617, 618 and proximal bores 620, 622. The nose cone dilator 610 may have an atraumatic tip 611.

Figure 12:
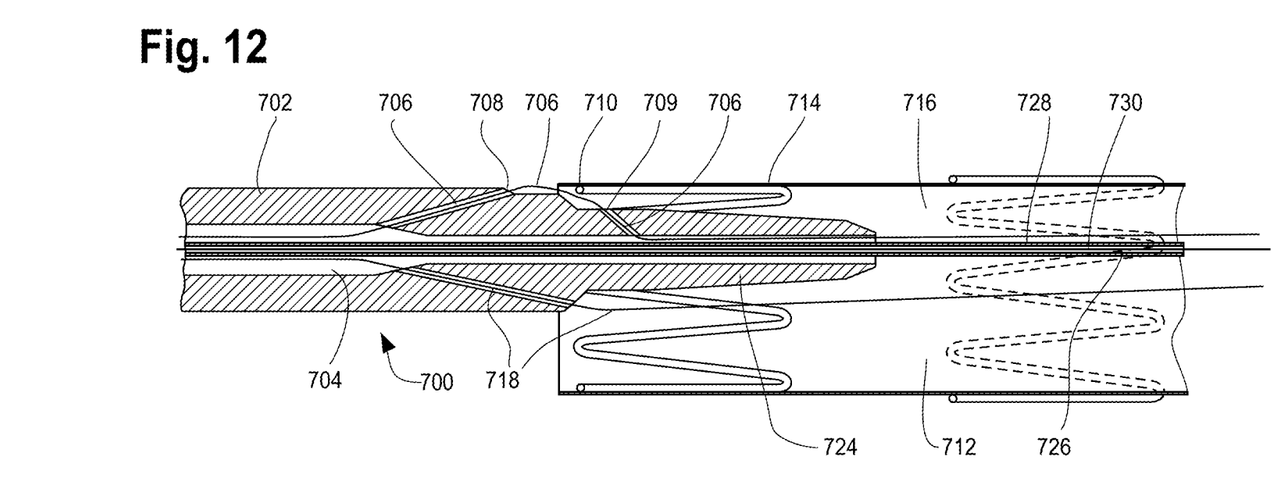
FIG. 12 shows a detailed view of a distal attachment mechanism for a distal trigger wire.
Figure 13:
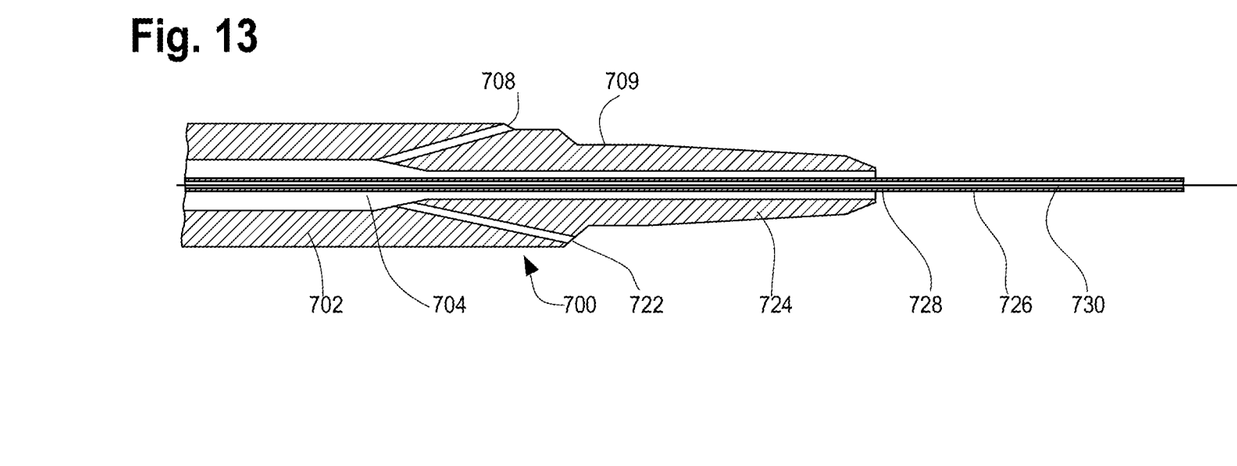
FIG. 13 is another view of the mechanism of FIG. 12.

FIGS. 12 and 13 show an alternative of (at the distal attachment region) of FIGS. 10 and 11. FIG. 12 shows the distal and proximal trigger wires in a partial view of the distal end of the delivery system 700, and FIG. 13 shows this view without the trigger wires in place. As shown, pusher 702 has an inner lumen 704. Distal trigger wire 706, or wires, extends through lumen 704 to distal bore 708 and exits the lumen 704. Trigger wire 706 then engages a distal attachment point 710 on the prosthesis 712 and then re-enters lumen through distal bore 709. The prosthesis 712, as shown has a distal most stent 714. The distal attachment point 710 may be on the stent 714 or on the graft 716. In this embodiment, proximal trigger wire 718, or wires, extends through lumen 704, exits through a distal bore 722 and then extends in the proximal direction toward the proximal attachment point and operates as described above in connection with FIGS. 10 and 11. The pusher may have a tapered proximal end 724 as shown. Further, extending through the lumen 704 is an inner cannula 726 having a guide wire lumen 728 to accommodate guide wire 730.

The present system eliminates the need for trigger wires to be held in place by knobs and the deployment steps of manually releasing the knobs and pulling the trigger wires. The system has the further advantage of providing a low profile delivery device and the release of the trigger wires in a single step or movement with reduced frictional forces.

Throughout this specification, various indications have been given as to preferred and alternative embodiments of the invention. However, it should be understood that the invention is not limited to these. It is therefore intended that the foregoing detailed description be regarded as illustrative rather than limiting.

The invention claimed is:

1. An endoluminal prosthesis delivery device comprising:
   a proximal end;
   a distal end;
   a prosthesis disposed at the proximal end of the delivery device and having a proximal end and a distal end;
   at least one trigger wire lumen;
   one or more proximal trigger wires disposed in the at least one trigger wire lumen and having a proximal end and a distal end, wherein the proximal end of the one or more proximal trigger wires is releasably secured to the proximal end of the prosthesis;
   one or more distal trigger wires disposed in the at least one trigger wire lumen and having a proximal end and a distal end, wherein the proximal end of the one or more distal trigger wires is releasably secured to the distal end of the prosthesis; a handle at the distal end of the delivery device;
   a housing at the distal end of the handle;
   a wire coiling assembly disposed in the housing, the wire coiling assembly comprising:
      a first spool secured to the distal end of the one or more proximal trigger wires;
      a second spool secured to the distal end of the one or more distal trigger wires;
   whereupon rotation of the first spool, the one or more proximal trigger wires is wound around the first spool and disengaged from the proximal end of the prosthesis and whereupon rotation of the second spool, the one or more distal trigger wires is wound around the second spool and disengaged from the distal end of the prosthesis.

2. The endoluminal prosthesis delivery device of claim 1, wherein the one or more proximal trigger wires comprises a plurality of trigger wires.

3. The endoluminal prosthesis delivery device of claim 1, wherein the at least one trigger wire lumen comprises a plurality of separate trigger wire lumens.

4. The endoluminal prosthesis delivery device of claim 3, wherein the one or more proximal trigger wires a disposed in a first lumen and the one or more distal trigger wires are disposed in a second lumen separate from the first lumen.

5. The endoluminal prosthesis delivery device of claim 1, further including a pusher extending from the handle and having a first distal bore from which the one or more distal trigger wires exits from the pusher to engage the distal end of the prosthesis.

6. The endoluminal prosthesis delivery device of claim 5, further including a second distal bore through which the one or more distal trigger wires re-enters the pusher.

7. An endoluminal prosthesis delivery device comprising:
   a proximal end;
   a distal end;
   a prosthesis disposed at the proximal end of the delivery device and having a proximal end and a distal end;
   a plurality of trigger wire lumens;
   one or more proximal trigger wires disposed in one of a plurality of trigger wire lumens and having a proximal end and a distal end, wherein the proximal end of the one or more proximal trigger wires is releasably secured to the proximal end of the prosthesis;
   one or more distal trigger wires disposed in another of the plurality of trigger wire lumens and having a proximal end and a distal end, wherein the proximal end of the one or more distal trigger wires is releasably secured to the distal end of the prosthesis; a handle at the distal end of the delivery device;
   a housing at the distal end of the handle;
   a wire coiling assembly disposed in the housing, the wire coiling assembly comprising:
      a first spool secured to the distal end of the one or more proximal trigger wires;
      a second spool secured to the distal end of the one or more distal trigger wires;
   whereupon rotation of the first spool, the one or more proximal trigger wires is wound around the first spool and disengaged from the proximal end of the prosthesis and whereupon rotation of the second spool, the one or more distal trigger wires is wound around the second spool and disengaged from the distal end of the prosthesis.

8. The endoluminal prosthesis delivery device of claim 7, further including a pusher extending from the handle and having a first distal bore from which the one or more distal trigger wires exits from the pusher to engage the distal end of the prosthesis.

9. The endoluminal prosthesis delivery device of claim 8, further including a second distal bore through which the one or more distal trigger wires re-enters the pusher.

* * * * *